United States Patent
Jutras et al.

(10) Patent No.: US 8,386,022 B2
(45) Date of Patent: Feb. 26, 2013

(54) MULTIFACETED TRACKER DEVICE FOR COMPUTER-ASSISTED SURGERY

(75) Inventors: Sébastien Jutras, Montréal (CA); Louis-Philippe Amiot, Hampstead (CA); Benoît Pelletier, Montréal (CA)

(73) Assignee: Orthosoft Inc., Montreal (CA)

( * ) Notice: Subject to any disclaimer, the term of this patent is extended or adjusted under 35 U.S.C. 154(b) by 1372 days.

(21) Appl. No.: 11/555,947

(22) Filed: Nov. 2, 2006

(65) Prior Publication Data

US 2007/0100325 A1    May 3, 2007

Related U.S. Application Data

(60) Provisional application No. 60/732,674, filed on Nov. 3, 2005.

(51) Int. Cl.
*A61B 5/05* (2006.01)
(52) U.S. Cl. .......................... 600/429; 600/407
(58) Field of Classification Search .................. 600/417, 600/424, 427, 429, 473; 606/130
See application file for complete search history.

(56) References Cited

U.S. PATENT DOCUMENTS

| | | | |
|---|---|---|---|
| 5,305,203 A | 4/1994 | Raab | |
| 5,663,795 A | 9/1997 | Rueb | |
| 5,792,147 A | 8/1998 | Evans et al. | |
| 5,961,456 A | 10/1999 | Gildenberg | |
| 6,021,343 A | 2/2000 | Foley et al. | |
| 6,122,538 A | 9/2000 | Sliwa, Jr. et al. | |
| 6,190,395 B1 | 2/2001 | Williams | |
| 6,285,902 B1 | 9/2001 | Kienzle, III et al. | |
| 6,402,762 B2 | 6/2002 | Hunter et al. | |
| 6,491,702 B2 | 12/2002 | Heilbrun et al. | |
| 6,517,478 B2 | 2/2003 | Khadem | |
| 6,675,040 B1* | 1/2004 | Cosman ........................ 600/427 |
| 6,856,828 B2 | 2/2005 | Cossette et al. | |
| 6,859,660 B2 | 2/2005 | Vilsmeier | |
| 6,990,220 B2 | 1/2006 | Ellis et al. | |
| 6,996,487 B2 | 2/2006 | Jutras et al. | |
| 7,166,114 B2 | 1/2007 | Moctezuma De La Barrera et al. | |
| 7,203,277 B2 | 4/2007 | Birkenbach et al. | |
| 2001/0034530 A1 | 10/2001 | Malackowski et al. | |
| 2002/1010752 | 8/2002 | Picard et al. | |
| 2004/0153191 A1* | 8/2004 | Grimm et al. ................. 700/114 |
| 2005/0049485 A1 | 3/2005 | Harmon et al. | |

(Continued)

FOREIGN PATENT DOCUMENTS

| CA | 2356271 | 7/2000 |
|---|---|---|
| CA | 2482006 | 10/2003 |

(Continued)

*Primary Examiner* — Long V. Le
*Assistant Examiner* — Nicholas Evoy
(74) *Attorney, Agent, or Firm* — Norton Rose Canada LLP

(57) ABSTRACT

A tracker device of the type is associated with a surgical instrument and being trackable in space by a CAS system such that a position of the surgical instrument is calculable. A support is adapted to be connected to the surgical instrument. Optical elements are mounted to the support in a first pattern so as to be detectable by the CAS system along a first range of visibility. Other optical elements are mounted to the support in a second pattern so as to be detectable by the CAS system along a second range of visibility, with the first range of visibility and the second range of visibility having at most a common portion, whereby a position of the surgical instrument is tracked within the first and the second range of visibility as a function of the detection of any one of the patterns of the optical elements.

13 Claims, 10 Drawing Sheets

U.S. PATENT DOCUMENTS

| | | |
|---|---|---|
| 2005/0215888 A1 | 9/2005 | Grimm et al. |
| 2006/0082546 A1 | 4/2006 | Wey |
| 2006/0173264 A1 | 8/2006 | Jansen |
| 2007/0073137 A1 | 3/2007 | Schoenfeld |
| 2007/0100325 A1 | 5/2007 | Jutras et al. |

FOREIGN PATENT DOCUMENTS

| | | |
|---|---|---|
| CA | 2487127 | 1/2004 |
| CN | 2662854 | 12/2004 |
| DE | 202005005085 | 8/2005 |
| EP | 1 444 962 | 8/2004 |
| EP | 1 769 768 | 4/2007 |
| FR | 2867376 | 9/2005 |
| WO | WO 99/38449 | 8/1999 |
| WO | WO-2005/070312 | 4/2005 |
| WO | WO-2005/104783 | 11/2005 |
| WO | WO-2005/104978 | 11/2005 |
| WO | WO-2006/050010 | 5/2006 |
| WO | WO-2006/106335 | 10/2006 |

\* cited by examiner

MULTIFACETED TRACKER DEVICE FOR COMPUTER-ASSISTED SURGERY

CROSS-REFERENCE TO RELATED APPLICATION

The present invention claims priority on U.S. Provisional Patent Application No. 60/732,674, filed on Nov. 3, 2005 by the present applicants.

BACKGROUND OF THE INVENTION

1. Field of the Invention

The present invention relates to computer-assisted surgery systems and, more particularly, to instrumentation used for the tracking of surgical tools during computer-assisted surgery.

2. Background Art

Tracking of surgical instruments or tools is an integral part of computer-assisted surgery (hereinafter CAS). The tools are tracked for position and/or orientation in such a way that information pertaining to bodily parts is obtained. The information is then used in various interventions with respect to the body, such as bone alterations, implant positioning, incisions and the like.

Two types of tracking systems are commonly used. The active tracking systems provide a transmitter on the tool to be tracked, which transmitter emits signals to be received by a processor of the CAS system, which will calculate the position and/or orientation of the tool as a function of the signals received. The transmitters of the active tracking systems are powered, for instance by being wired to the CAS system or by being provided with an independent power source, so as to emit signals.

Passive tracking systems do not provide active transmitters on the tools, and therefore represent fewer issues pertaining to sterilization. The CAS system associated with passive tracking has an optical sensor apparatus provided to visually detect optical elements on the tools. The optical elements are passive, whereby no power source is associated therewith.

In order to obtain values for position and/or orientation, the optical elements must be in the line of sight of the optical sensor apparatus. Accordingly, with passive tracking systems, surgery takes place in a given orientation as a function of the required visibility between the optical sensor apparatus and the optical elements.

In a known embodiment, the optical elements are retro-reflective spheres detectable by the optical sensor apparatus of the CAS system. The retro-reflective spheres are positioned in a recognizable pattern, such that position and/or orientation information of the tool associated with the optical elements is calculable. The geometry of the retro-reflective spheres advantageously offers a good range of visibility. However, the retro-reflective spheres are relatively costly to produce.

SUMMARY OF INVENTION

It is therefore an aim of the present invention to provide a tracker device that addresses issues pertaining to the prior art.

Therefore, in accordance with the present invention, there is provided a tracker device of the type being associated with a surgical instrument and being trackable in space by a CAS system such that at least a position of the surgical instrument is calculable, comprising: a support adapted to be connected to the surgical instrument; at least two optical elements mounted to the support in a first pattern so as to be detectable by the CAS system along a first range of visibility; and at least two other optical elements mounted to the support in a second pattern so as to be detectable by the CAS system along a second range of visibility, with the first range of visibility and the second range of visibility having at most a common portion; whereby at least a position of the surgical instrument is tracked within the first and the second range of visibility as a function of the detection of any one of the patterns of the optical elements.

Further in accordance with the present invention, there is provided a computer-assisted surgery system for tracking surgical instruments during surgery, comprising: at least one surgical instrument; a tracker device secured to the surgical instrument, the tracker device having a first geometrical pattern of optical elements visible along a first range of visibility, and a second geometrical pattern of optical elements visible along a second range of visibility; a tracking system having a sensor unit tracking any one of the geometrical patterns as the instrument is moved with the first range of visibility and/or the second range of visibility, a database storing geometrical pattern data and instrument/tracker device relation data, and a position and orientation calculator connected to the sensor unit and to the database to identify the geometrical pattern being tracked from the geometrical pattern data, and to calculate a position and orientation of the tracker device as a function of the tracking of the identified geometrical pattern from the sensor unit; the tracking system calculating a position and orientation of the instrument as a function of the position and orientation of the tracker device and of the instrument/tracker device relation data.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figure 1:
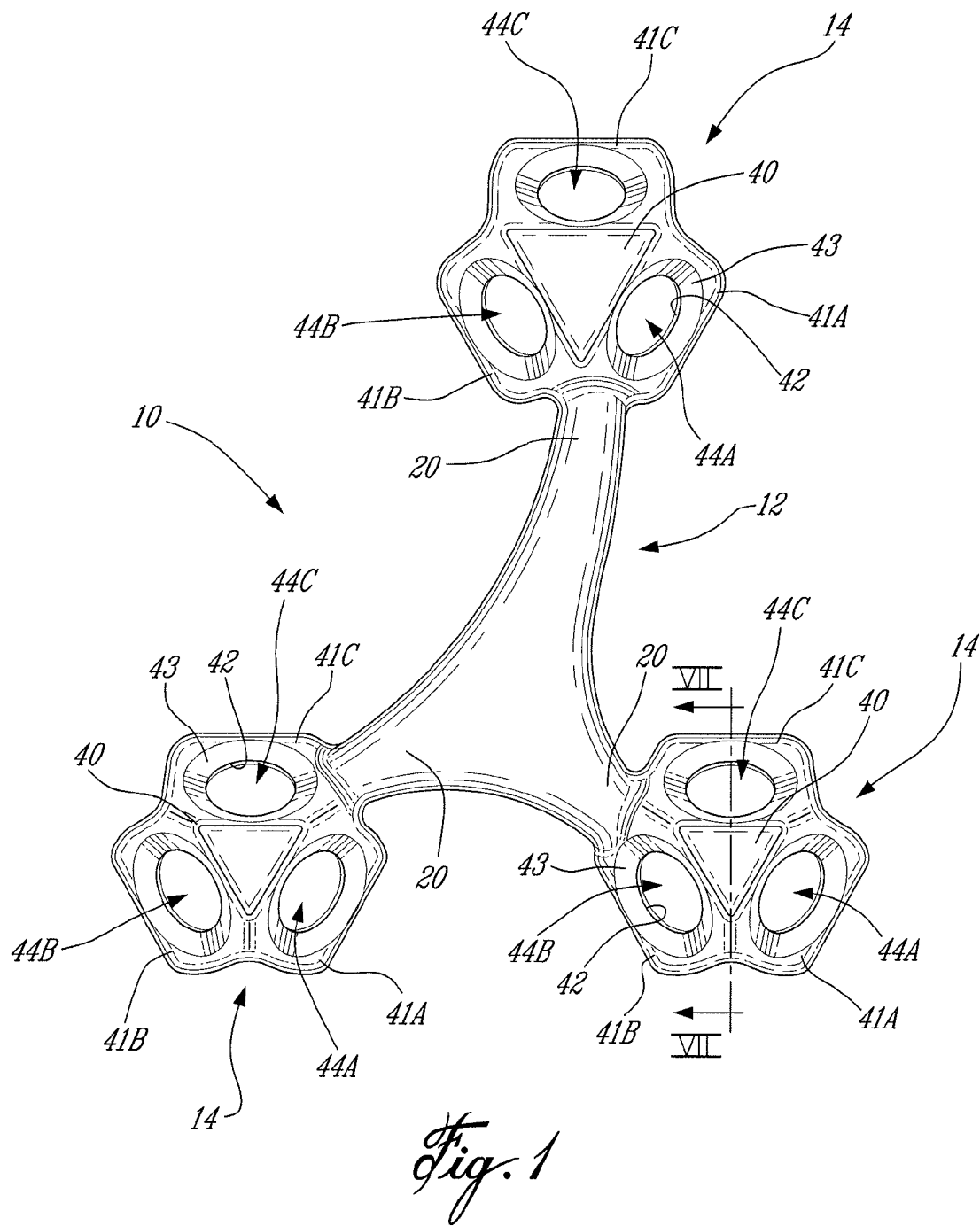
FIG. 1 is an elevation view of a multifaceted tracker device constructed in accordance with an embodiment of the present invention.
Figure 4:
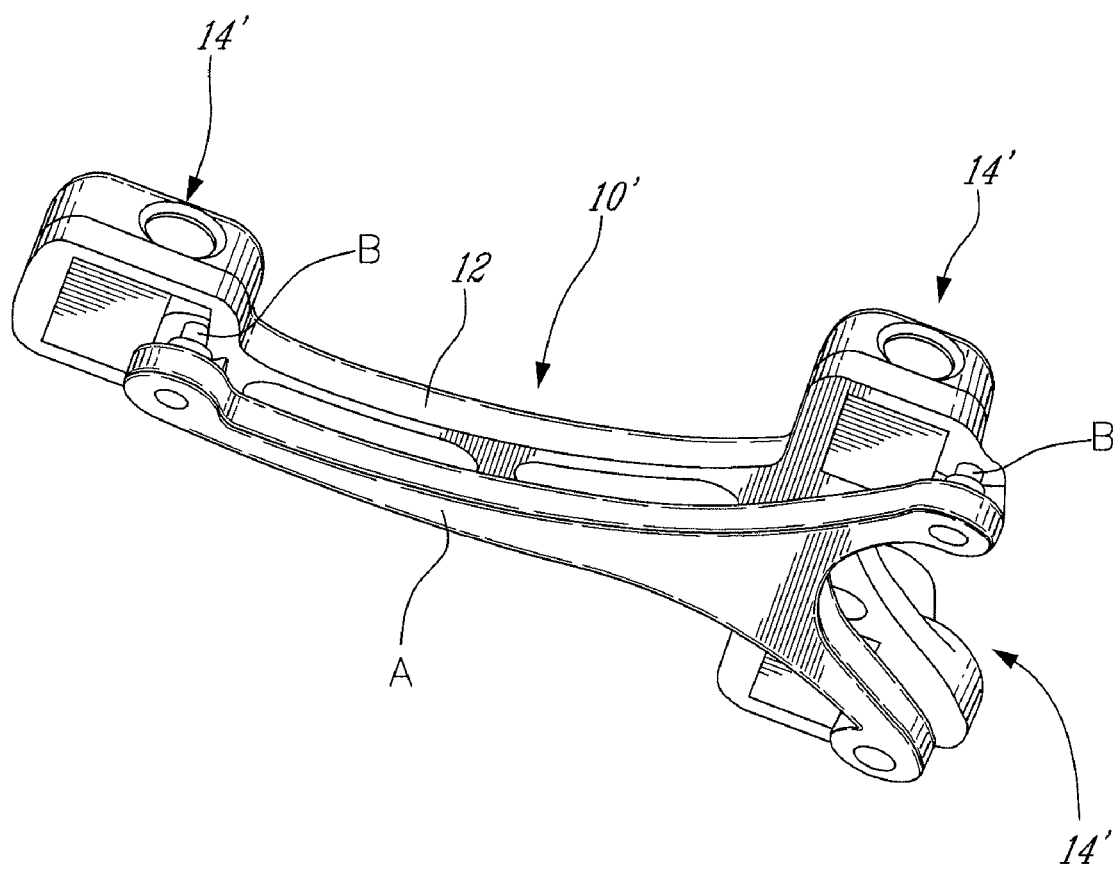
FIG. 4 is a perspective view illustrating a multifaceted tracker device constructed in accordance with another embodiment of the present invention, being connected to a passive tracker support.
Figure 6:
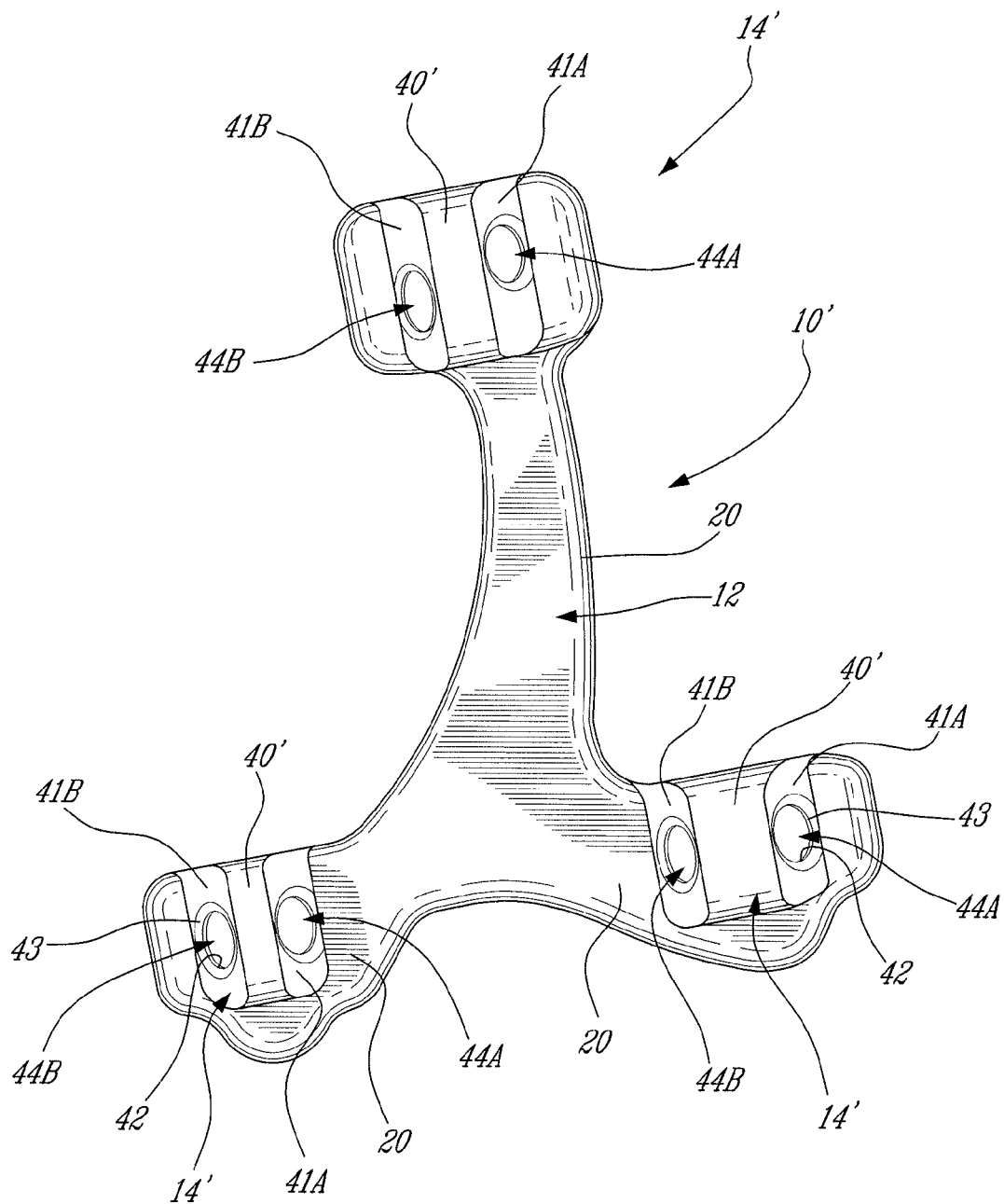
FIG. 6 is an elevation view of the multifaceted tracker device of FIG. 4.

Referring now to the drawings and more particularly to FIG. 1, a multifaceted tracker device in accordance with an embodiment is generally shown at 10, whereas another embodiment of the tracker device is shown at 10' in FIGS. 4 and 6. Yet another embodiment is shown at 10" in FIGS. 8 and 9. The tracker device 10 has a support 12 and tracker ends 14.

The support 12 is provided to interrelate the tracker device 10 to a surgical tool (e.g., registration pointer, rasp, drill guide, reference base or like instruments used in CAS). The support 12 supports the tracker ends 14 in a given geometry, such that an optical sensor apparatus of a CAS system visually recognizes the patterns. With the tracking of the patterns of the tracker ends 14, the CAS system calculates a position and/or orientation of the surgical instrument or tool associated with the tracker device 10.

The tracker ends 14 support the optical elements that constitute the geometrical patterns and are thus visually detectable by the optical sensor apparatus of the CAS system.

Figure 2:
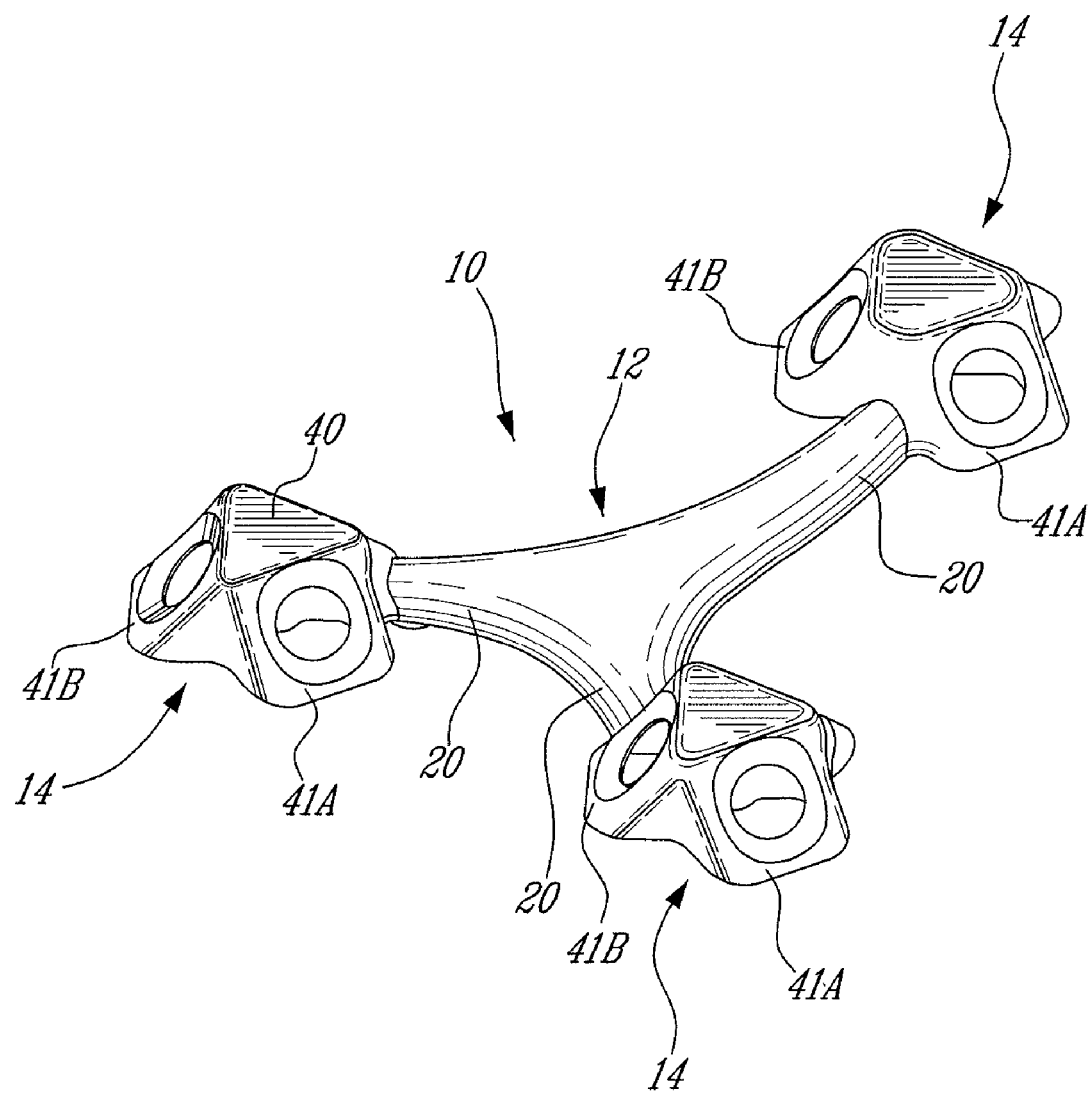
FIG. 2 is a perspective view of the multifaceted tracker device of FIG. 1, from a front view standpoint.
Figure 3:
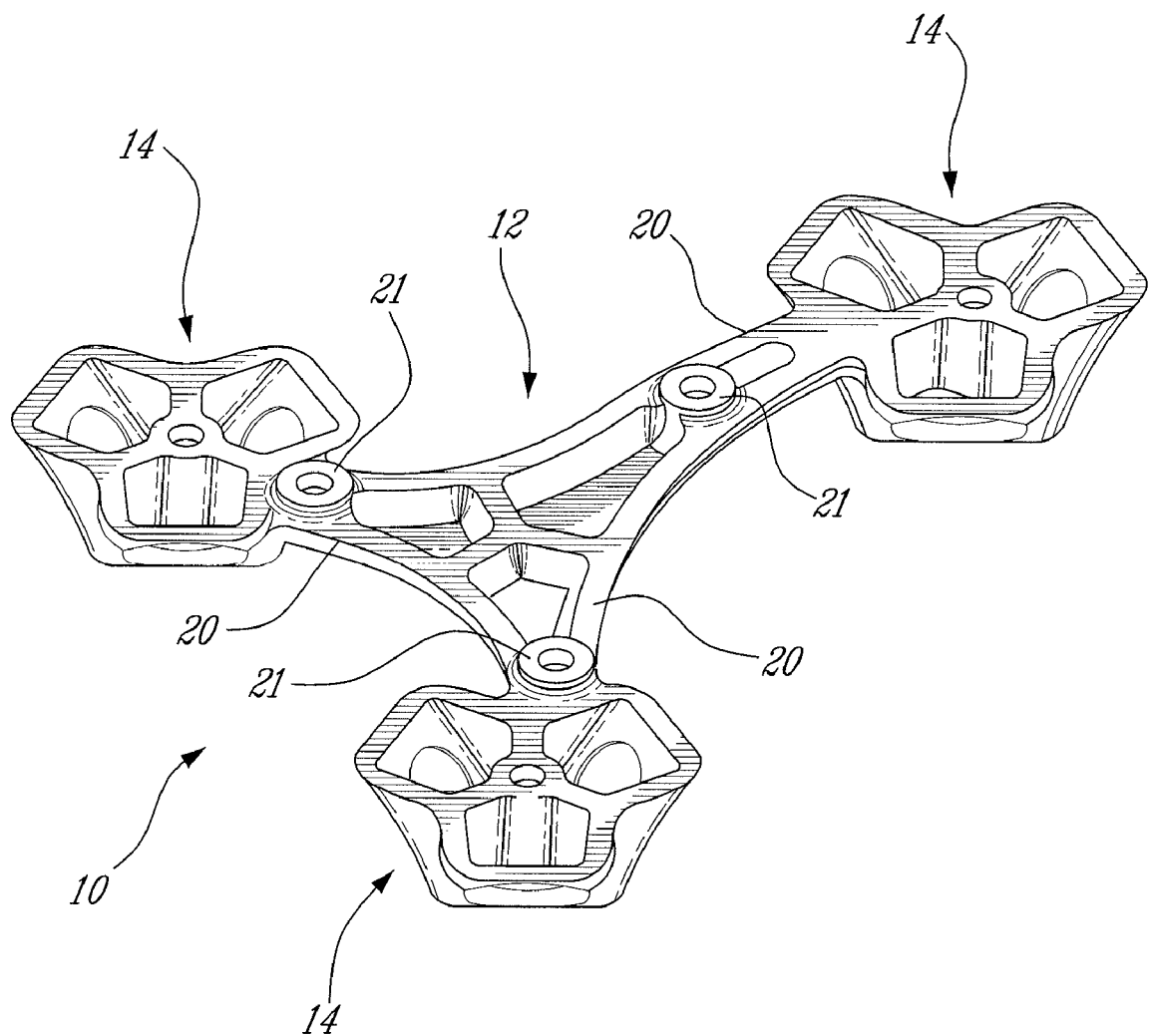
FIG. 3 is a perspective view of the multifaceted tracker device of FIG. 1, from a rear view standpoint.

Referring to FIGS. 1 to 3, the support 12 is shown having three arms 20. The arms 20 converge centrally, and each have at a free end one of the tracker ends 14. As seen in FIG. 3, female connectors 21 are provided in an underside of the support 12, and may alternatively be provided in an undersurface of the tracker ends 14.

Accordingly, as seen in FIG. 4, a tracker device 10', generally similar to the tracker device 10 of FIGS. 1 to 3, may be connected to the support A of a surgical tool. The support A is of the type having three male connectors, two of which are shown at B. The male connectors B are snap-type fingers provided to support detectable spheres on the support A. It is pointed out that such a three-point connection between the support A and the tracker device 10/10' ensures a structural strength to the tracker device 10/10'.

Therefore, in an embodiment, the tracker device 10/10'/10" (FIGS. 8 and 9) can be used with the existing supports A of surgical tools. It is however contemplated to provide alternative types of connection systems to connect the tracker device 10/10'/10" to surgical tools.

In order for an object to be tracked in space for position and orientation, at least two points associated with the object must be known. With two points, the object can be tracked for position and orientation under specific conditions (e.g., object and the two tracked points being collinear, and no view interruption after calibration). A geometrical pattern of three nonlinear trackable points is commonly used for six-degree-of-freedom tracking, and more trackable points can be used for increased precision in the tracking.

Figure 5:
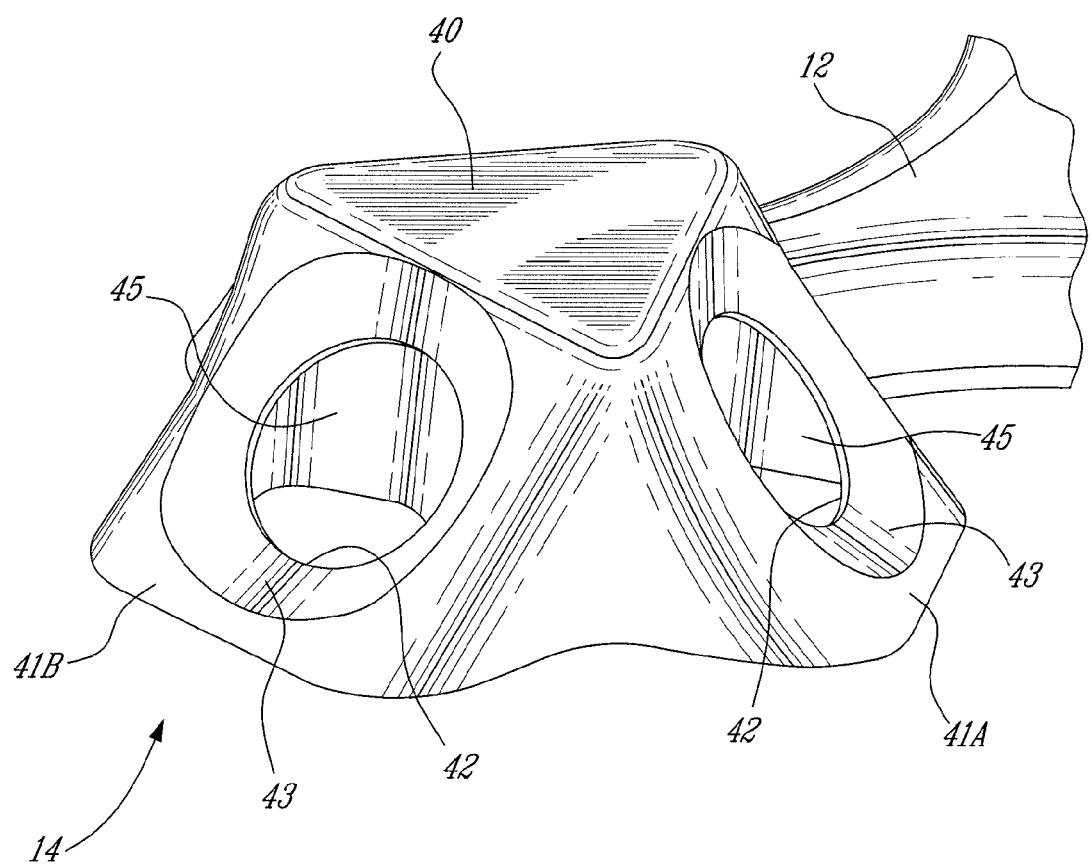
FIG. 5 is a perspective view, enlarged, of a tracker end of the multifaceted tracker device of FIG. 1.

Accordingly, in the embodiment of FIG. 1, the three tracker ends 14 are provided in three sets of three detectable elements. Referring concurrently to FIGS. 1 and 5, the tracker ends 14 are each provided with a pyramidal body 40 having faces 41A, 41B and 41C (hereinafter faces 41 unless otherwise indicated). The faces 41 each define an opening 42 having a given geometrical shape. In the embodiment of FIGS. 1 and 5, the given geometrical shape is a circle. Beveled surfaces 43 are provided in the faces 41 and enclose the openings 42.

Retro-reflective surfaces are positioned in the openings 42, so as to form circular optical elements 44A, 44B, and 44C, respectively provided in the faces 41A, 41B, and 41C of the tracker ends 14. Other shapes are also considered for the optical elements 44. The retro-reflective surfaces are made of a retro-reflective material that will be detected by the optical sensor apparatus associated with the CAS system. For instance, the material Scotch-Lite™ is suited to be used as retro-reflective surface.

As the optical elements 44 must be in a given geometrical pattern to be recognized by the optical sensor apparatus of the CAS system, the optical elements 44 are regrouped in one embodiment in sets of three. Referring to FIG. 1, a first set of three elements 44 consists of the optical elements 44A, each of which is in a different one of the tracker ends 14. Similarly, a second set consists of the elements 44B, and a third set consists of the elements 44C.

In the embodiment of FIG. 1, each of the elements of a same set (e.g., the first set of elements 44A) are parallel to a same plane. Accordingly, the elements 44A are visible from a same field of view.

The sets of elements 44 are strategically positioned with respect to one another so as to optimize a range of visibility of the tracker device 10. More specifically, the sets are positioned such that once the optical sensor apparatus of the CAS system loses sight of one of the sets, another set is visible. This ensures the continuous tracking of the tracking device 10 within a given range of field of view.

The sets each form a geometrical pattern that is recognized by the optical sensor apparatus of the CAS system. The combination of circular openings 42 and retro-reflective surface gives a circular shape to the optical elements 44. According to the angle of view of the optical sensor apparatus, these circles will not always appear as being circular in shape. Therefore, the position of the center of the circles can be calculated as a function of the shape perceived from the angle of view by the optical sensor apparatus.

In the embodiment of FIG. 1, the geometrical pattern therefore consists of a triangle defined by the centers of the optical elements 44 of the sets. It is preferred that the three triangles of the three different sets of optical elements 44 be of different shape, with each triangle being associated with a specific orientation with respect to the tool. Alternatively, the three triangles formed by the three different sets may be the same, but the perceived shape of the circular reflective surfaces 44 must be used to identify which of the three sets of reflective surfaces 44 is seen.

Although triangular geometrical patterns are illustrated, it is contemplated to use other geometrical patterns, such as lines and various polygonal shapes.

It is pointed out that a calibration of the surgical tool with the tracker device 10 thereon is preferably performed prior to the use of the tracker device 10, to calibrate a position and/or orientation of each of the detectable geometrical patterns with respect to the tool. In order to optimize the range of visibility of the tracker device 10, the arrangement of the circular optical elements 44 on a tracker end 14 is taken into consideration.

Referring to FIG. 6, a multifaceted tracker device in accordance with another embodiment is generally shown at 10'. The multifaceted tracker device 10' and the multifaceted tracker device 10 have similar parts, whereby like parts will bear like reference numerals.

Tracker ends 14' of the tracker device 10' differ from those of the tracker device 10 in that each of the tracker ends 14' only has two circular optical elements 44, namely sets of three elements 44A and of three elements 44B. Accordingly, the tracker device 10' offers a smaller range of visibility when compared to the tracker device 10.

Figure 7:
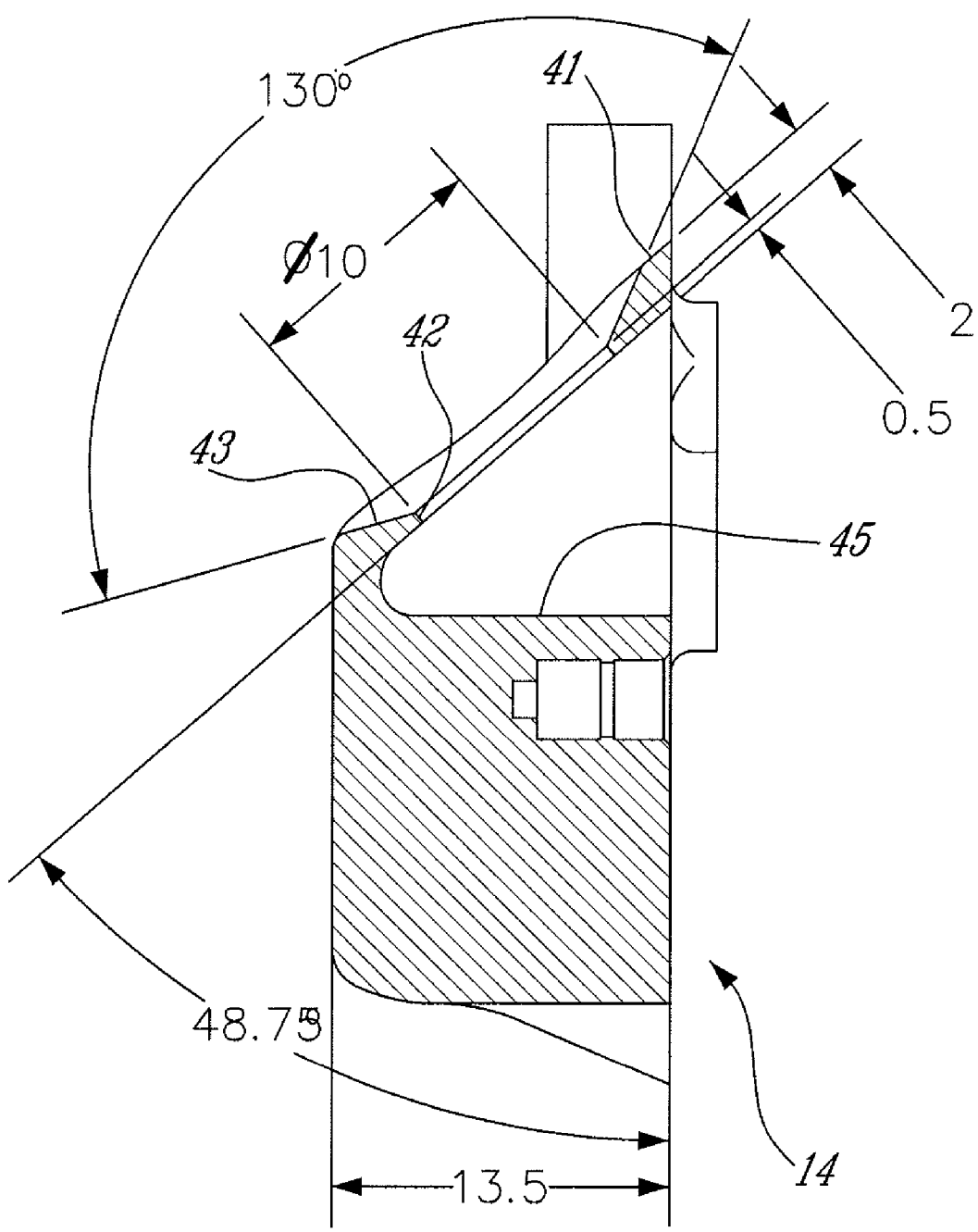
FIG. 7 is a cross-sectional view of a tracker end taken along cross-section line VII-VII of FIG. 1.

It is contemplated to change the retro-reflective material used to make up the optical elements 44. More specifically, as shown in FIG. 7, the tracker ends 14 are illustrated as having cavities 45 opposite the openings 42, so as to accommodate throwaway patches of retro-reflective material. Accordingly, the support 12 and emptied tracker ends 14 can be sterilized to be reused, with new retro-reflective patches being inserted into the tracker ends 14. As a function of the contemplated use of the tracker end 10 (e.g., reusable, disposable), the support 12 and emptied tracker ends 14 are molded in plastic or cast in metal. Other materials are considered. The surgical instrument may be disposable as well. For instance, the surgical instrument may be integrally molded with the tracker device 10/10', for single use.

Depending on the contemplated type of surgery, some of the sets of optical elements 44 may not be required. For instance, in some types of surgical intervention, a broad range of visibility may not be required, whereby some of the openings 42 may not be provided with retro-reflective material.

It is pointed out that the beveled surfaces 43 are provided to set the retro-reflective material back from the faces 41. This represents one way of reducing the risk of contact between bodily tissue and the retro-reflective material. Bodily substances may interfere with the reflectivity of the retro-reflective material.

Figure 8:
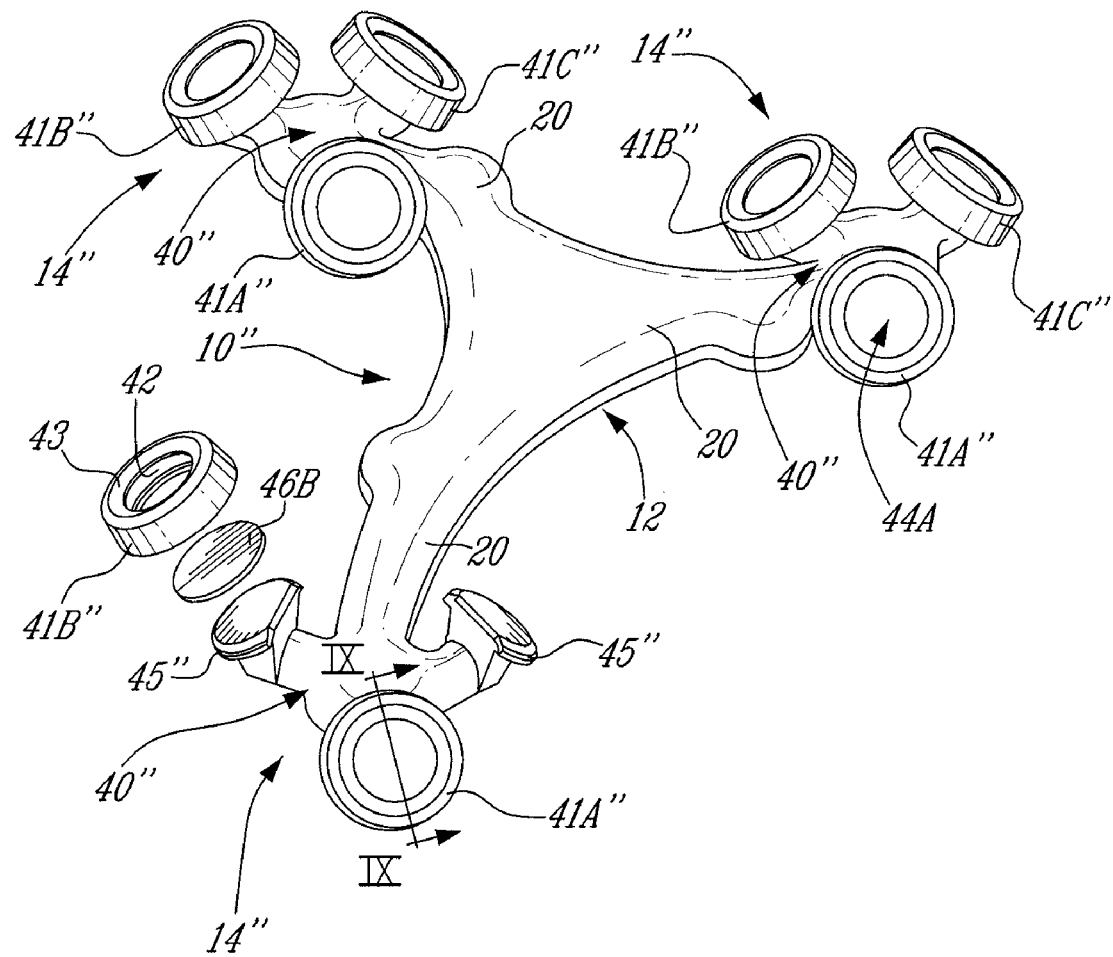
FIG. 8 is a perspective view of a multifaceted tracker device constructed in accordance with another embodiment of the present invention.
Figure 9:
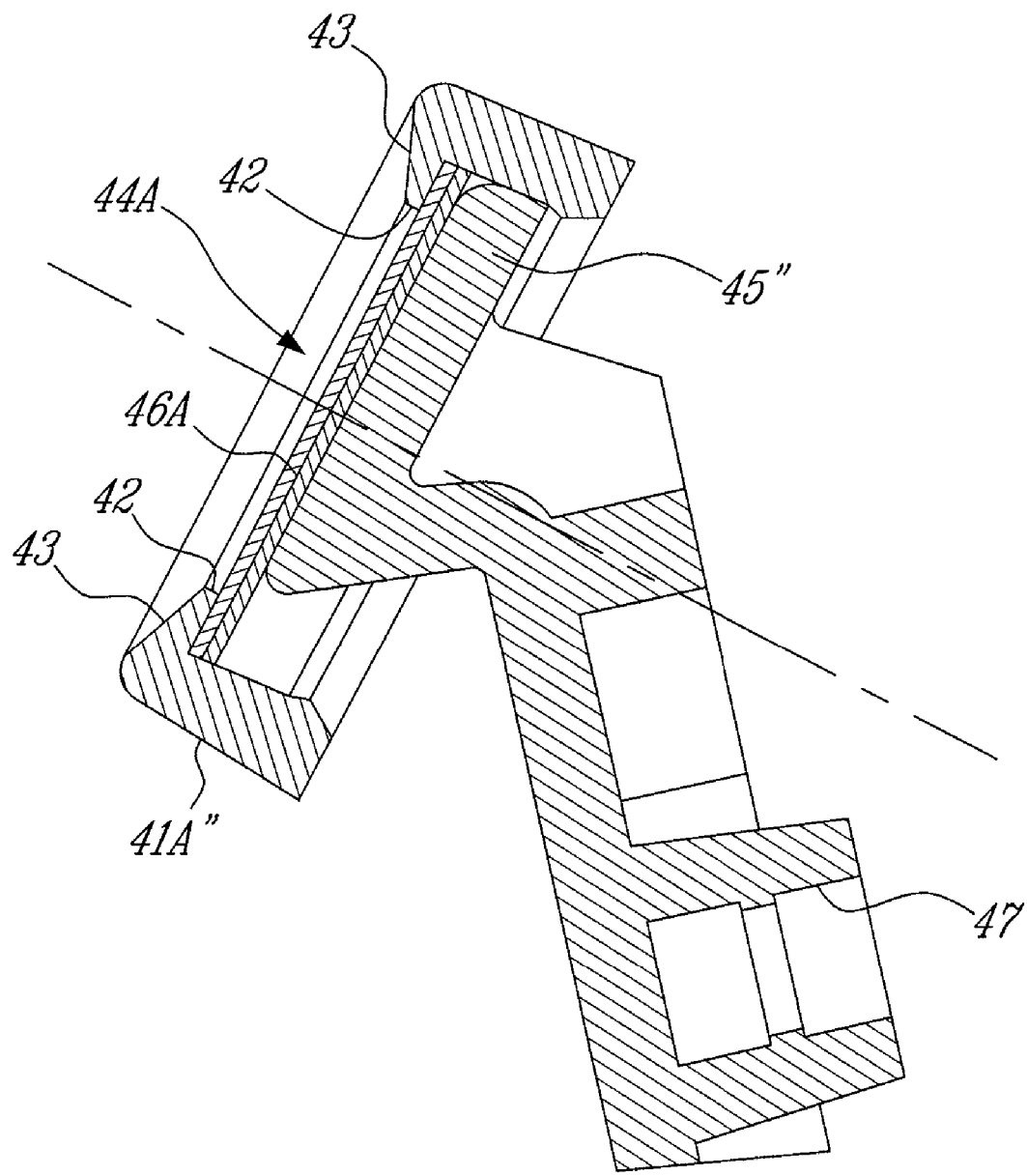
FIG. 9 is a cross-sectional view of a tracker end taken along cross-section line IX-IX of FIG. 8.

Referring to FIGS. 8 and 9, the tracker device 10" is shown in greater detail. The multifaceted tracker device 10" and the multifaceted tracker devices 10/10' (FIGS. 1 to 7) have similar parts, whereby like parts will bear like reference numerals.

The tracker device 10" is similar to the tracker device 10 (FIGS. 1 to 3), in that the tracker device 10" has three optical elements 44 per tracker end 14". However, the tracker ends 14" of the tracker device 10" are provided with three-legged structures 40" as opposed to pyramidal bodies 40 for the tracker device 10.

Each of the three-legged structures 40" has three legs, each of which defines an optical element 44 (i.e., 44A, 44B and 44C). Each leg has an annular cap 41" (i.e., 41A", 41B"), that has an opening 42 and a beveled surface 43. The cap 41" releasably snaps onto a flanged support 45". A token 46 of reflective material (i.e., 46A, 46B, 46C) is held captive between the cap 41" and the support 45", and defines the optical element 44 with the periphery of the opening 42.

After surgery, the cap 41" is removed, and the token 46 of reflective material is thrown away or sterilized. The cap 41" is sterilized or thrown away, and the support 12 is sterilized for subsequent use.

As shown in FIG. 9, the tracker ends 14" of the tracker device 10" each have a female connector 47 for being snap-fitted to male connectors of a support, such as the support 12. The tracker device 10" has a first set of female connectors 21 set up as illustrated in FIG. 3 on the arms 20, and a second set, with the female connectors 47, that represents a larger triangle, for larger supports 12. Accordingly, the devices 10" can be used for two different sizes of support 12. This feature can be used with the devices 10 and 10' as well.

Moreover, the tracker ends 14/14'/14" can be used without a common support 12, as long as the tracker ends 14/14'/14" are aligned to a specific position when connected to the male connectors B of the support A.

Figure 10:
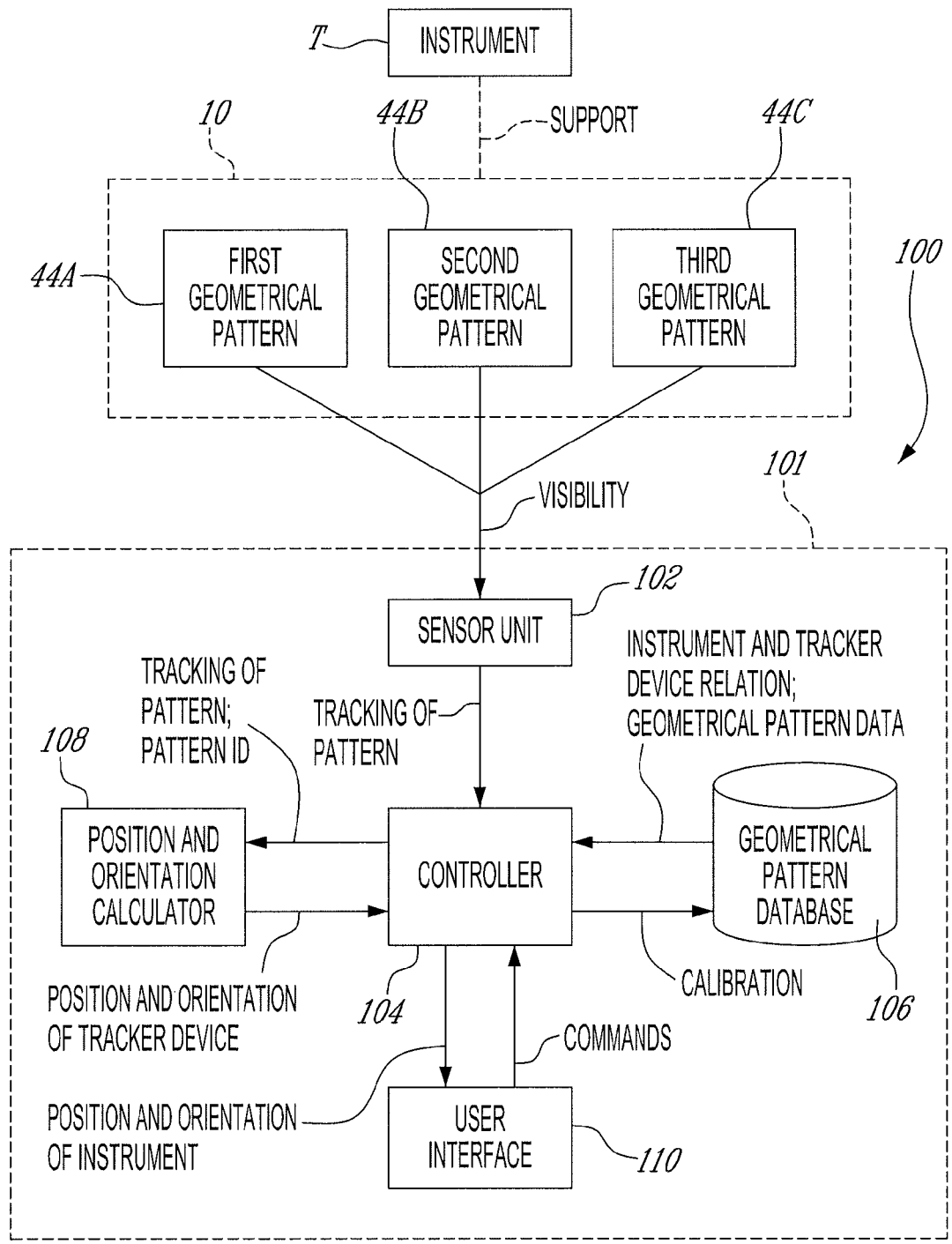
FIG. 10 is a block diagram of a computer-assisted surgery system using the multifaceted tracker device of any one of FIGS. 1 to 9.

Referring to FIG. 10, a computer-assisted surgery system using the tracker device 10 is generally illustrated at 100. The computer-assisted surgery system 100 incorporates the tracker device 10, as secured to a surgical instrument T by way of a support. In accordance with FIGS. 1 to 9, the tracker device 10 provides two or three different geometrical patterns, namely patterns 44A, 44B and 44C. As described previously, each of the patterns 44A, 44B and 44C is associated with a given range of visibility. Although the tracker device 10 of FIG. 10 is illustrated, the trackers 10' and 10" are also used with the computer-assisted surgery system 100.

The computer-assisted surgery system has a tracking system 101, which is typically a computer having a processor. The tracking system 101 has a sensor unit provided in order to visually track the optical elements of the patterns 44A to 44C. Typically, the sensor unit 102 involves a pair of sensors (e.g., Navitrack™).

A controller 104 is connected to the sensor unit 102. Therefore, the controller 104 receives the tracking of patterns from the sensor unit 102.

A database 106 is provided so as to store the geometrical pattern data. More specifically, the various patterns of the tracker device 10 are stored in the database 106. Similarly, the relation between the instrument and the tracker device is stored in the database 106. The instrument/tracker device relation may result from a calibration performed in the first steps of use of the computer-assisted surgery system.

A position and orientation calculator 108 is associated with the controller 104. The position and orientation calculator 108 receives the tracking of patterns from the sensor unit 102, as well as the geometrical pattern data. Therefore, the position and orientation calculator 108 identifies which one of the patterns of the tracker device 10 is being tracked. With the identification of the pattern being tracked, the position and orientation calculator calculates the position and orientation of the tracker device 10.

The position and orientation of the tracker device 10 is sent to the controller 104. The controller 104 will combine this information with the instrument/tracker device relation from the geometrical pattern database 106, so as to calculate the position and orientation of the instrument T. This information is sent to the user interface 110, such that the user of the computer-assisted surgery system obtains information pertaining to the position and orientation of the instrument T in the various forms known to computer-assisted surgery (e.g., visual representation, numerical values such as angles, distances, etc.). It is pointed out that the database 106 may as well be part of the controller 104 or the position and orientation calculator 108.

The invention claimed is:

1. A tracker device of the type being associated with a surgical instrument and being trackable in space by a CAS system such that at least a position of the surgical instrument is calculable, comprising:

a support adapted to be connected to the surgical instrument and supporting at least four different optical elements;

at least three optical elements each having a single flat retro-reflective surface and being mounted to the support in a first pattern so as to be detectable by the CAS system along a first range of visibility, with the first pattern defining a first polygon with each corner of the first polygon being a point in a respective one of the three optical elements; and at least three other optical elements separate from said three optical elements, the at least three other optical elements each having a single flat retro-reflective surface and being mounted to the support in a second pattern, with the second pattern defining a second polygon geometrically different from the first polygon, with each corner of the second polygon being a point in a respective one of the three other optical elements so as to be detectable by the CAS system along a second range of visibility, with the first range of visibility and the second range of visibility having at most a common portion;

whereby at least a position of the surgical instrument is tracked within the first and the second range of visibility as a function of the detection and identification of any one of the first polygon and the second polygon of the optical elements.

2. The tracker device according to claim 1, wherein the flat retro-reflective surfaces of the at least three optical elements are on separate planes and parallel to a same first plane, and the flat retro-reflective surfaces of the at least three other optical elements are on separate planes and parallel to a same second plane, the first plane and the second plane being solely in an unparallel relation.

3. The tracker device according to claim 2, wherein the first polygon has three of the at least three optical elements in a first triangle, and the second polygon has three of the at least three other optical elements in a second triangle, whereby the surgical instrument is trackable for position and orientation.

4. The tracker device according to claim 1, further comprising at least three further other optical elements mounted to the support in a third pattern, with the third pattern defining a third polygon geometrically different from the first polygon and the second polygon, with each corner of the third polygon being a point in a respective one of the three further other optical elements so as to be detectable by the CAS system along a third range of visibility, with the third range of visibility and at least one of the first range and the second range of visibility having at most a common portion.

5. The tracker device according to claim 1, wherein each optical element is formed by an annular cap secured to the support, and a reflective member with the flat retro-reflective surface held captive to the support by the annular cap, an opening in the annular cap being opposite the reflective member so as to define a geometry of the optical element.

6. The tracker device according to claim 5, wherein the annular cap is releasably secured to the support so as to change reflective members after use.

7. The tracker device according to claim 5, wherein the reflective members are each in a concavity defined by the annular cap, so as to be protected from accidental contact.

8. The tracker device according to claim 7, wherein the concavity has a beveled surface surrounding the reflective member to increase a range of visibility of the reflective member.

9. The tracker device according to claim 1, wherein each of the optical elements is circular.

10. The tracker device according to claim 1, wherein the support has a first connection configuration so as to be releasably connected to a first size of surgical instrument, and a second connection configuration so as to be releasably connected to a second size of surgical instrument.

11. A computer-assisted surgery system for tracking surgical instruments during surgery, comprising:
at least one surgical instrument;
a tracker device secured to the surgical instrument, the tracker device having at least six optical elements, with a first geometrical pattern of at least a first, a second and a third optical elements visible along a first range of visibility, with the first geometrical pattern defining a first polygon with each corner of the first polygon being a point in a respective one of the three optical elements, and a second geometrical pattern of at least a fourth, a fifth and a sixth optical elements separate from the first, the second and the third optical elements and visible along a second range of visibility, with the second pattern defining a second polygon geometrically different from the first polygon, with each corner of the second polygon being a point in a respective one of the three other optical elements;
a tracking system having:
a sensor unit tracking a visible one of the geometrical patterns depending on which of the first range of visibility and the second range of visibility is in a line of sight of the sensor unit as the instrument is moved;
a database storing geometrical pattern data and instrument/tracker device relation data; and
a position and orientation calculator to identify either one of the geometrical pattern being tracked from the geometrical pattern data, and to calculate a position and orientation of the tracker device as a function of the tracking of the identified geometrical pattern from the sensor unit; the tracking system calculating a position and orientation of the instrument as a function of the position and orientation of the tracker device and of the instrument/tracker device relation data.

12. The computer-assisted surgery system according to claim 11, wherein the instrument/tracker device relation data is obtained by calibration.

13. The computer-assisted surgery system according to claim 11, wherein the tracker device has a third geometrical pattern of a seventh, an eighth and a ninth optical elements visible along a third range of visibility, with the third pattern defining a third polygon geometrically different from the first polygon and the second polygon, with each corner of the third polygon being a point in a respective one of the three further other optical elements.

* * * * *